(12) United States Patent
Stearns et al.

(10) Patent No.: US 7,311,866 B1
(45) Date of Patent: Dec. 25, 2007

(54) METHOD FOR CREATING A MOLD FOR A KNEE BRACE AND A KNEE BRACE

(75) Inventors: Jeffrey B. Stearns, Hopatcong, NJ (US); Juan B. Paez, Rockaway, NJ (US)

(73) Assignee: EBI, L.P., Parsippany, NJ (US)

( * ) Notice: Subject to any disclaimer, the term of this patent is extended or adjusted under 35 U.S.C. 154(b) by 755 days.

(21) Appl. No.: 10/603,477

(22) Filed: Jun. 25, 2003

Related U.S. Application Data

(60) Provisional application No. 60/391,995, filed on Jun. 25, 2002.

(51) Int. Cl.
*B29C 33/38* (2006.01)

(52) U.S. Cl. .................. 264/219; 29/458; 264/101; 264/222; 264/313; 264/320; 264/500

(58) Field of Classification Search ............... 264/222, 264/101, 313, 320, 219, 500; 29/458
See application file for complete search history.

(56) References Cited

U.S. PATENT DOCUMENTS

| | | | | |
|---|---|---|---|---|
| 4,575,805 A | * | 3/1986 | Moermann et al. | 700/163 |
| 4,672,955 A | * | 6/1987 | Cooper | 602/5 |
| 5,009,223 A | * | 4/1991 | DeFonce | 602/16 |
| 5,042,464 A | * | 8/1991 | Skwor et al. | 602/16 |
| 5,334,135 A | * | 8/1994 | Grim et al. | 602/26 |
| 5,433,418 A | * | 7/1995 | Nowak et al. | 249/139 |
| 5,601,852 A | * | 2/1997 | Seemann | 425/112 |
| 5,658,244 A | * | 8/1997 | Townsend et al. | 602/26 |
| 6,423,019 B1 | * | 7/2002 | Papay et al. | 602/17 |
| 6,620,510 B1 | * | 9/2003 | Taguchi et al. | 428/413 |
| 7,048,704 B2 | * | 5/2006 | Sieller et al. | 602/16 |
| 2002/0179240 A1 | * | 12/2002 | Clemens et al. | 156/307.1 |
| 2003/0144620 A1 | * | 7/2003 | Sieller et al. | 602/5 |
| 2004/0068215 A1 | * | 4/2004 | Adelson et al. | 602/26 |

\* cited by examiner

*Primary Examiner*—Allan R. Kuhns
(74) *Attorney, Agent, or Firm*—Harness, Dickey & Pierce, P.L.C.

(57) ABSTRACT

Disclosed is a method for producing a three-dimensional composite structure and a method for producing the mold for the three-dimensional composite structure. The mold is formed of at least one rigid die member and a second thermoplastic die member. The second thermoplastic die member is formed by coupling a rubber flexible pattern to a surface of the first die member. Vacuum or pressure is applied to a heated thermoplastic sheet to cause the heated thermoplastic sheet to deform about the flexible pattern, thereby forming the second die. Strips of reinforced polymer thermoset pre-preg material are then positioned within the cavities formed by the flexible pattern and are allowed to cure. Optionally, heat, pressure, and vacuum may be applied to the mold construction to facilitate the curing of the thermoset materials.

18 Claims, 19 Drawing Sheets

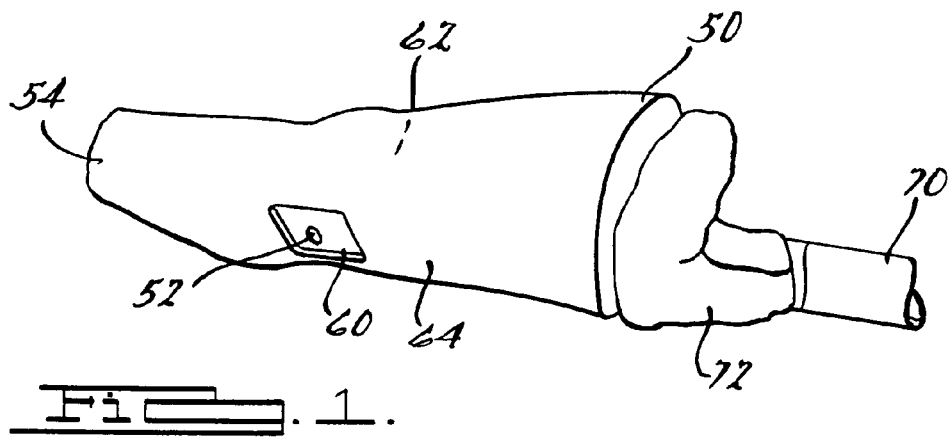
FIG. 1.
FIG. 2.
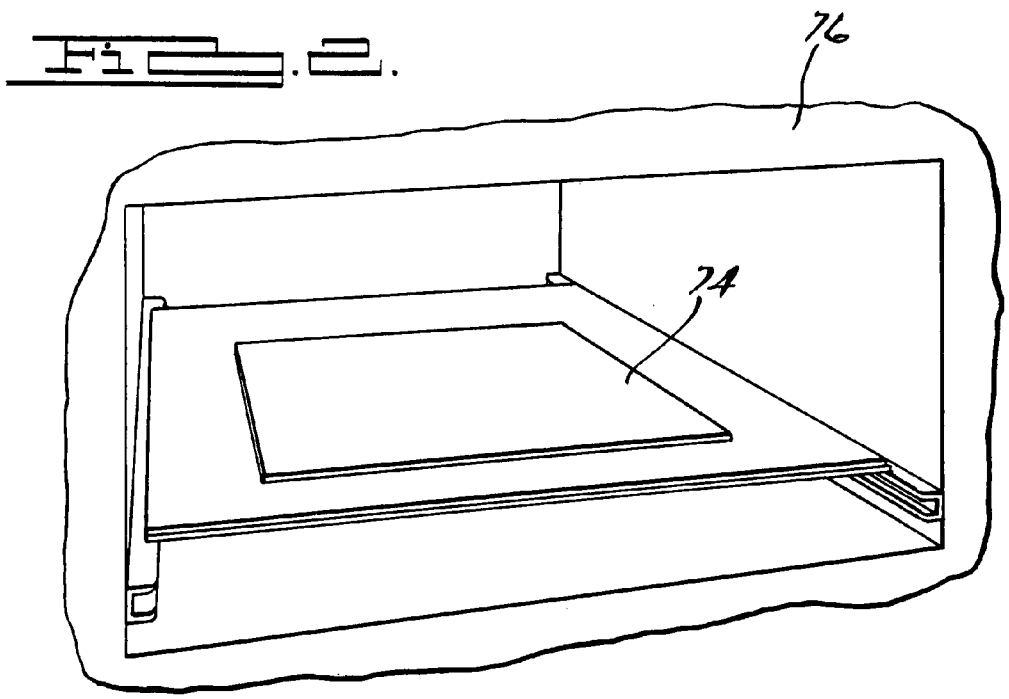
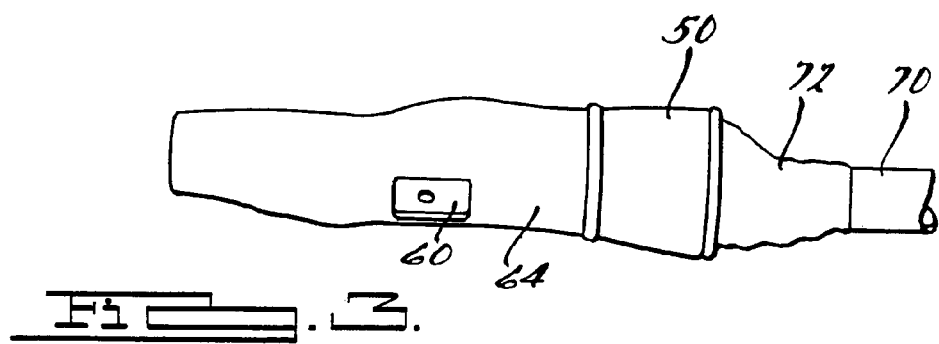
FIG. 3.

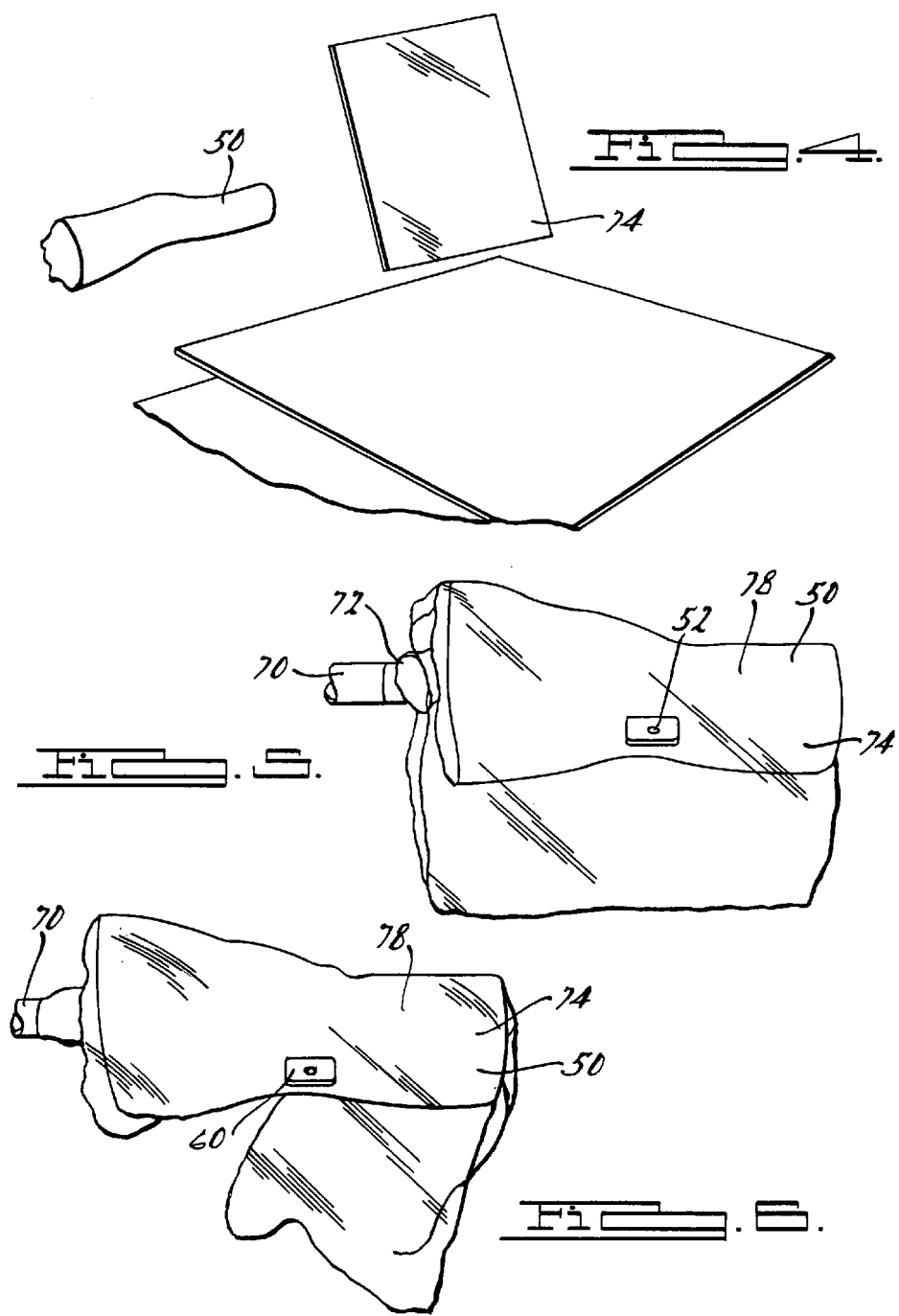

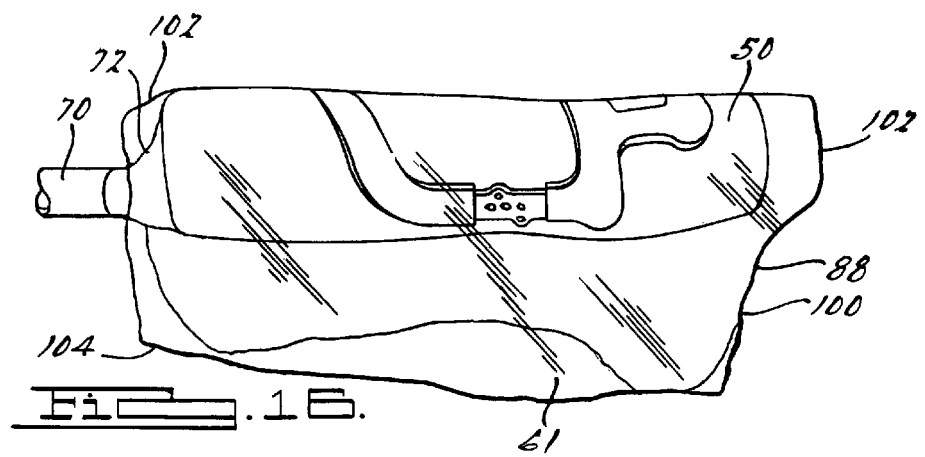
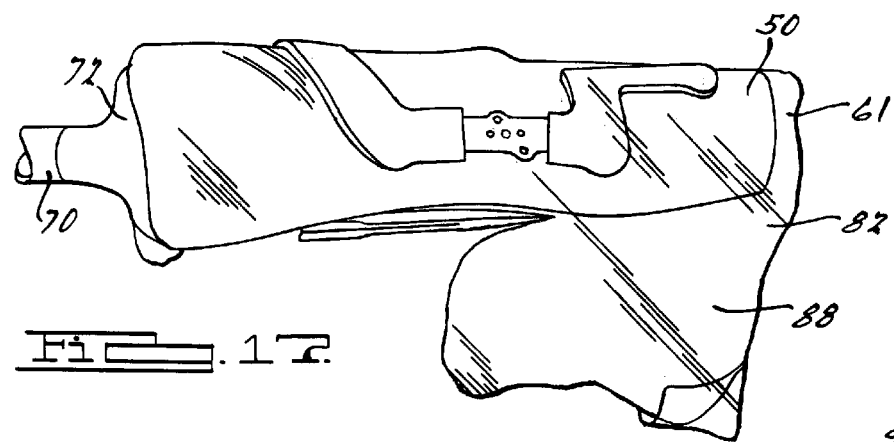
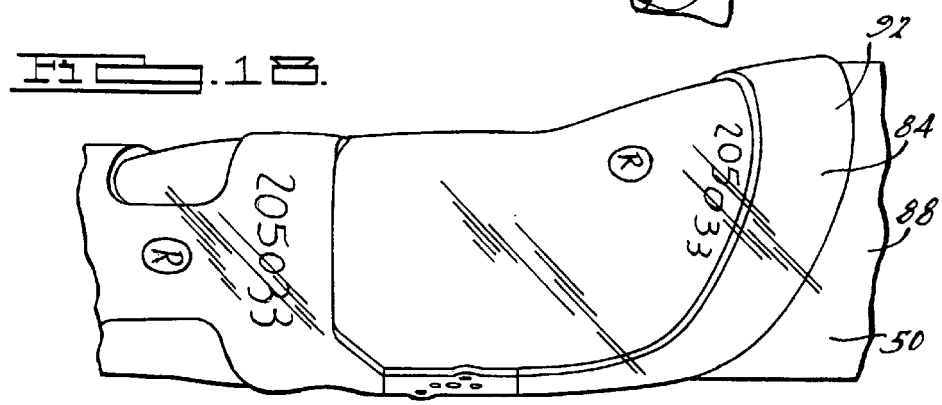

US 7,311,866 B1

METHOD FOR CREATING A MOLD FOR A KNEE BRACE AND A KNEE BRACE

This application claims the benefit of U.S. Provisional Application No. 60/391,995, filed on Jun. 25, 2002. The disclosure of the above application is incorporated herein by reference.

FIELD OF THE INVENTION

The present invention relates generally to composite materials and to methods of manufacturing the composite materials. In particular, the methods of manufacturing the composite materials of the present invention include a method of creating a mold, and more particularly, a method produce a three dimensional mold for use in forming a customized composite knee brace.

BACKGROUND OF THE INVENTION

It is known that knee braces can be produced by the use of composite materials are coupled together by metallic hinges. Typically, complex three-dimensional die cavities are formed by complex cuttings of metal die materials. These die cavities correspond to the leg shape as well as to the exterior shape of the leg brace. Obviously, these tools are very expensive and time consuming to produce. As such, the use of customized composite leg braces is significantly limited.

SUMMARY OF THE INVENTION

Accordingly, it is an object of the present invention to provide a method of manufacturing the composite material which includes creating a custom mold. The method produces an three dimensional mold having a thermoplastic die for use in forming a customized thermoset composite knee brace.

In one embodiment of the present invention, a method for producing a three-dimensional composite support structure for a body is provided. The method begins with a coupling of a flexible pattern to an exterior surface of a three-dimensional model of the body. The model of the body and the flexible pattern are then coated with a deformable polymer layer. Either gas pressure or a vacuum is applied to the polymer layer so as to cause an imprint of the flexible pattern to be formed onto the polymer layer, thereby forming a cavity in the polymer layer when the flexible pattern is removed. The polymer layer is then allowed to harden into a splash mold. Strips of reinforced polymer thermoset pre-preg material are positioned into the flexible pattern of the splash mold. The splash mold is then re-coupled to the model of the body and pressure and/or vacuum are applied to the model and the splash molds in the presence of heat so as to cure the reinforced polymer pre-preg material.

In another embodiment of the present invention, a method for producing a custom knee brace is disclosed. The method comprises providing a three-dimensional model of a knee and leg structure. A flexible pattern corresponding to a portion of the knee brace is positioned on the surface of the knee model. The knee model and flexible pattern are then covered with a deformable polymer layer. Pressure or vacuum is applied to the polymer layer so as to cause an imprint of the flexible pattern onto the polymer layer. The polymer layer is allowed to harden into a splash mold. The splash mold of the knee brace is removed from the model and strips of reinforced polymer thermoset pre-preg material is positioned into the imprint of the flexible mold. The splash mold and thermoset pre-preg are then coupled to the model of the knee. Either gas pressure or vacuum are applied to the splash mold in the presence of heat so as to cure the reinforced polymer material.

In yet another embodiment of the present invention, a die for a reinforced composite structure is disclosed. The die comprises a first die member having a first die surface, and a second die member being formed of a thermoplastic material having a second die surface. The first and second die surfaces define a cavity configured to mold thermoset polymer materials.

In yet another embodiment of the present invention, a method for producing a die for reinforced thermoset polymer materials is disclosed. The method comprises providing a mold base having a first die surface. A flexible die pattern is positioned onto the first die surface. A heated thermoplastic splash mold sheet is positioned over the first die surface and the flexible pattern. Pressure or vacuum are applied to the thermoplastic sheet to cause it to deform over the flexible pattern, thereby forming a cavity conforming to the shape of the flexible pattern. The thermoplastic sheet is then cooled until it is solid and removed from the mold base to form the second die member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 depicts a customized molded plaster cast according to the teachings of the present invention;

FIG. 2 teaches the preparation of offset material used according to the present invention;

FIG. 3 depicts the application of a stockinet over a cast model;

FIGS. 4-6 depict the application of the offset material to the cast model according to the teachings of the present invention;

FIGS. 16-18 depict the formation of a splash mold according to the teachings of the present invention;

FIGS. 44-46 depict the preparation of the mold prior to autoclaving; and

DETAILED DESCRIPTION OF THE PREFERRED EMBODIMENTS

Figure 7:
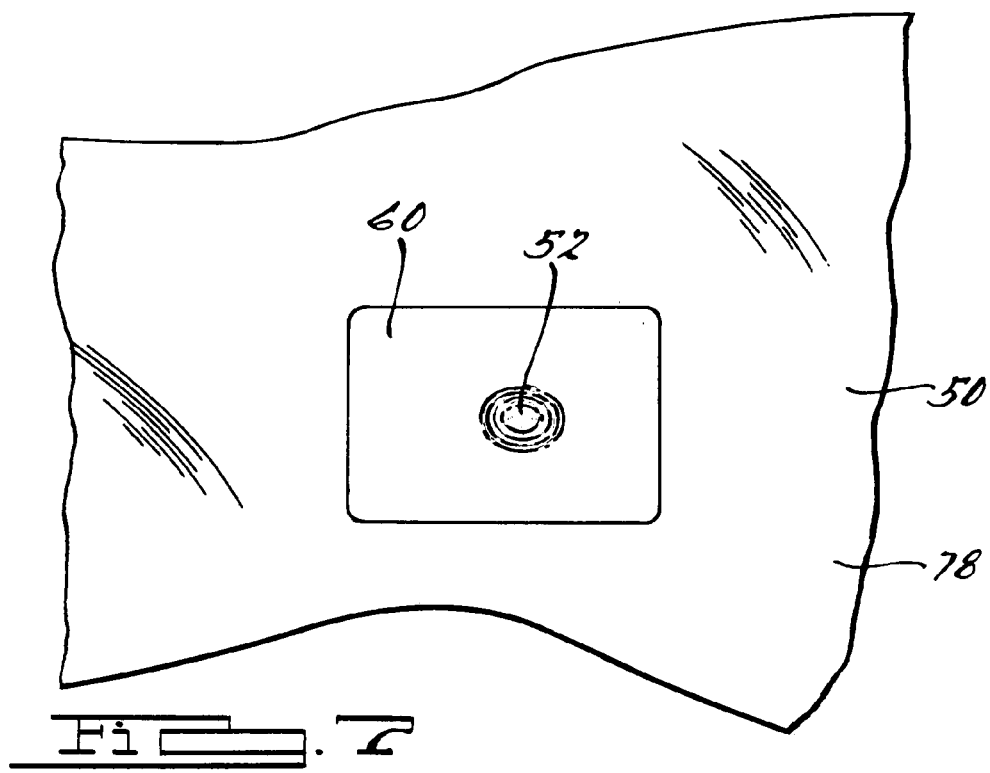
FIGS. 7 and 8 depict the offset material over the cast model according to the teachings of the present invention.

The following description of the preferred embodiment is merely exemplary in nature and is in no way intended to limit the invention, its application, or uses. Specifically, described is a method for forming three dimensional composite structure. Whereas the three dimensional structure described is a knee brace, the application of these principles are equally applicable to any number of three dimensional composite structures formed of thermoset or thermoplastic polymers.

FIG. 1 depicts a customized plaster cast model 50 according to the teachings of the present invention. The custom plaster cast model 50 is formed from a negative cast (not shown) of a patient's extremity, which is provided by a treating physician. This negative cast has important landmarks, such as a joint rotational axis 52, called out. Typically, the cast model 50 of a knee will be about 20" long, and specifically, plus and minus 10" in the proximal and distal directions from the axis of rotation 52 of the joint.

Upon receipt of the negative cast, the three-dimensional cast model 50 of the joint is produced. The exterior surface 54 of the cast model can be modified prior to the formation of the three-dimensional composite structure 56. Offsets or cutouts and landmarks and fixation points can be formed into the exterior surface 54 of the cast model 50. For example, to produce a knee brace 58, a pair of generally parallel planes 60 are formed on the medial and lateral sides 62 and 64 of a knee joint. These parallel planes 60 are used to align a pair of knee braces' parallel knee joint hinges 66. Additionally, a hole 68 is bore into the cast model 50 at the axis of rotation 52 of a knee joint.

Optionally, the cast model 50 can be formed of urethane foam which is shaped utilizing computer bioscanning system. The computerized bioscanning system creates a three dimensional computer model of the patients leg utilizing lasers. The lasers scan the plaster cast provided by the physicians. The three dimensional computer model is then modified to provide Offsets or cutouts and landmarks and fixation points. A 5-axis cutting tool can be coupled to the computer to produce the model 50 which is used to form the composite structure.

As can be seen in FIG. 1, the cast model 50 is positioned onto an integral support member 70. In this instance, the support member 70 is a hollow aluminum tube which is configured to support the cast model 50 as well as to draw a vacuum during processing as is described in further detail below. Coupled to and disposed about the support member is a flexible seal 72, which is used to seal a vacuum enclosure about the cast model 50 during various processing steps.

FIG. 2 shows a sheet of thermoplastic material 74 disposed within an oven 76. The thermoplastic material 74 is coupled the surface of the cast model 50 and functions as a constant thickness offset layer 78 from the exterior surface 54 of the cast model 50. Specifically, the offset layer 78 functions to provide the gap and spacing needed between the knee brace 58 and the patient's leg for soft internal knee brace structures. It is envisioned that the thickness of the offset layer 78 can be adjusted in the different areas along the cast model 50 to allow for different spacing of a solid brace and the surface of the patient's skin. Specifically, different thicknesses can be used in areas where increased padding or hinge thickness is necessary.

The thermoplastic material 74 shown is a ⅛" layer of polyethylene material. Both sides of the polymer offset layer 78 are cleaned with alcohol and checked for defects. The polymer offset layer 78 is then placed in an oven 76 having a temperature of 400° F. maximum. At this point, three layers of stockinet 80 are positioned over the cast model 50. A knot is tied to the stockinet 80 and trimmed to the length of the cast model 50. The stockinet 80 functions as an air passage between the cast model 50 and the polymer offset layer 78 during processing.

As best seen in FIG. 4, the polymer offset layer 78 is removed from the oven 76 after it turns clear (approximately 5 minutes). The polymer offset layer 78 is transported to the cast model 50 and is subsequently applied over the stockinet layers. As best seen in FIG. 5, the bottom 82 and ends 84 of the polymer offset layer 78 are sealed. A vacuum is drawn through the support member 70 to pull the polymer offset layer 78 onto the surface of the stockinet 80 disposed about the cast model 50. FIG. 6 depicts the trimming away of the polymer offset layer 78.

Figure 8:
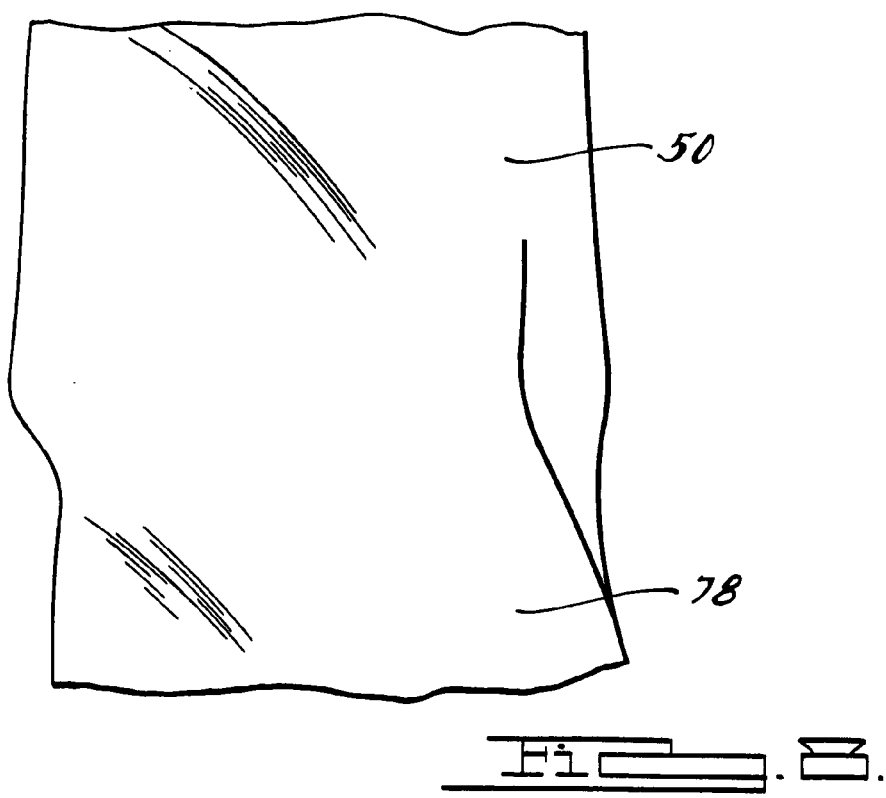

FIGS. 7 and 8 show the polymer offset layer 78 disposed over the cast model 50. As can be seen, modifications formed on the exterior surface 54 of the cast model 50 are transferred to the outer surface of the offset. FIG. 7 shows the flattened hinge accepting portions 60 as well as the bore defined at the knee joint rotation axis 52.

Figure 9:
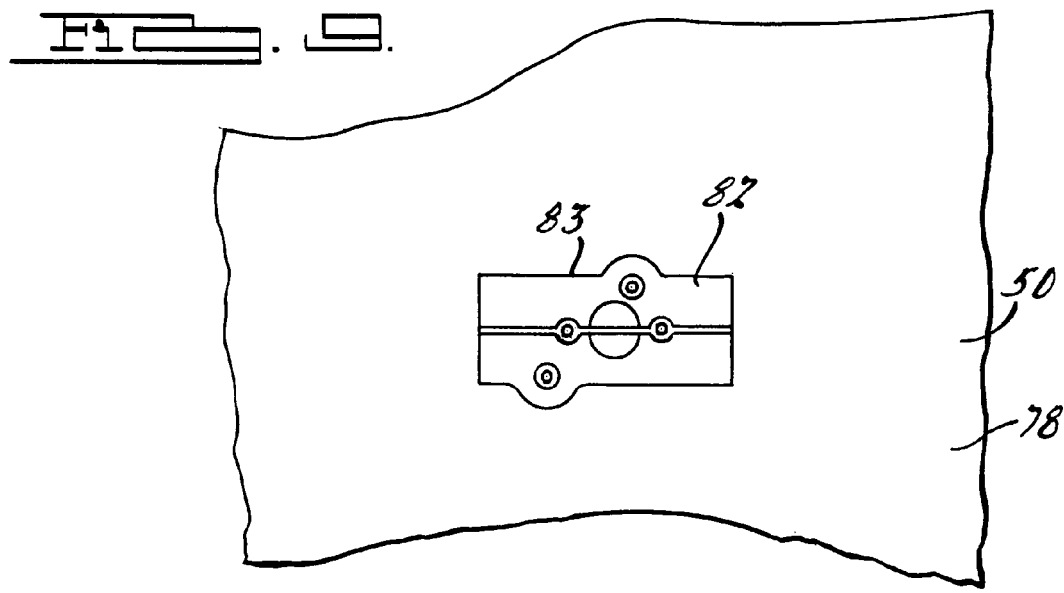
FIG. 9 depicts positioning a hinged template onto a rotational axis of the cast model according to the teachings of the present invention.
Figure 10:
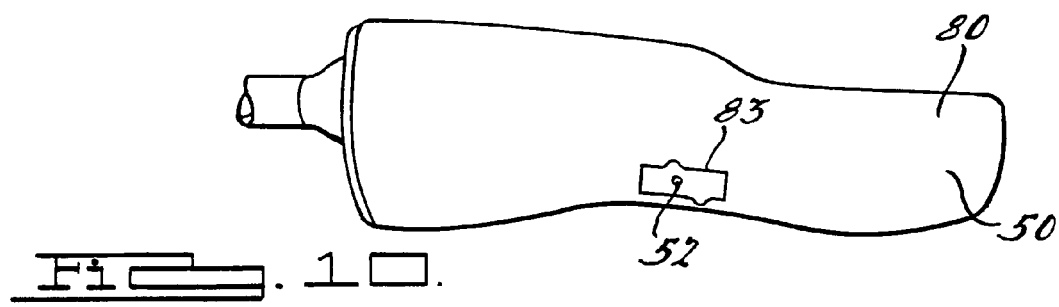
FIG. 10 depicts the cast model coated by a stockinet according to the teachings of the present invention.

FIG. 9 depicts the fixation of a hinge jig 82 into the knee axis hole. The hinge jig 82 is aligned along the rotational axis 52 of the leg and is traced with a marker to form a hinge pattern outline 83. FIG. 10 depicts the pattern outline 82 of the hinge jig 82 about the knee hole axis. The hinge pattern outline 83 is used to align flexible patterns 84, which will eventually define a three dimensional composite frame 86.

Two layers of stockinets 80 are then applied over the polymer offset layer 78. Upon the application of each stockinet 80, the ankle end of the stockinet 80 is tied into a knot while the thigh end is trimmed to fit the length of the casting. The stockinet 80 material functions as an air passage way between the offset layer 78 and a thermoplastic layer 88 which will form a thermoplastic splash mold 90.

Figure 11:
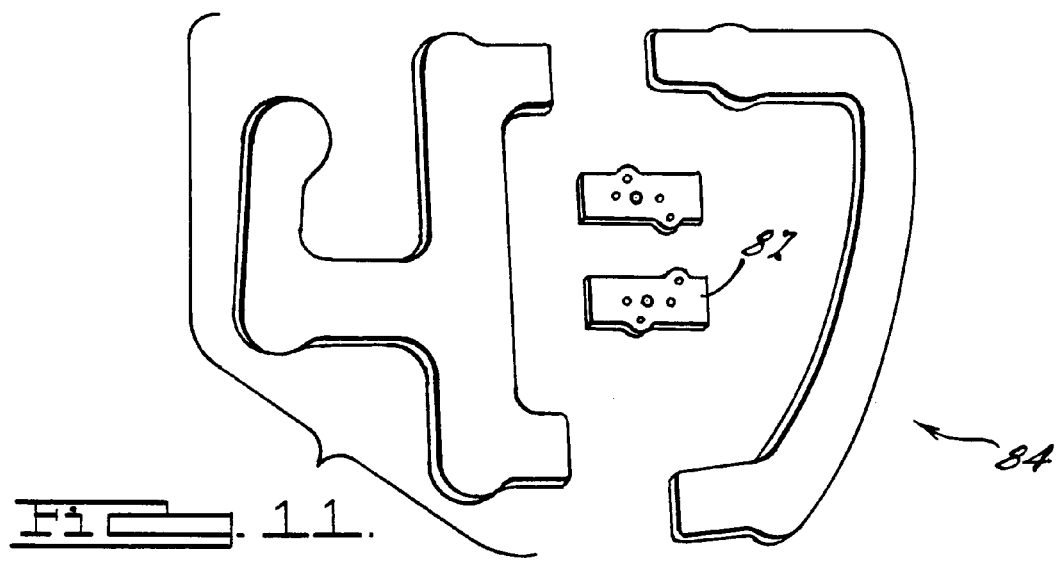
FIG. 11 depicts flexible templates used to produce the knee brace.

FIG. 11 depicts a set of flexible patterns 84 which will be applied to the cast model 50. The flexible patterns 84 are formed of polyurethane material or silicon having a durometer of about 10, but can be any compressible elastic material which maintains is configuration under processing parameters. It should be noted that a full set of thigh 92 and calf 94 patterns are available. The process of the present invention allows for the intermingling of different flexible thigh 92 and calf 94 patterns as are required by the specific geometry of the cast model 50.

Figure 12:
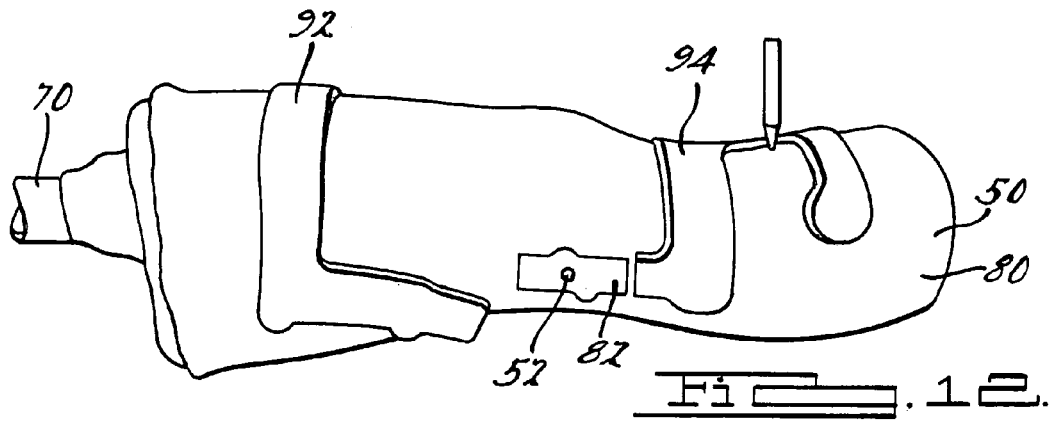
FIGS. 12-15 depict the application of the flexible templates to the cast model.

FIG. 12 depicts the application of the flexible patterns 84 onto the cast model 50. First, a thigh pattern 92 that fits the leg is chosen and placed onto the cast model 50. The traced hinge jig 82 is used to align the flexible pattern 84 onto the cast model 50. A tracing of the thigh pattern 92 is then made onto the stockinet 80. A flexible calf pattern 94 is chosen and placed onto the cast model 50. Again, the flexible calf pattern 94 is aligned with the exterior profile of the hinge jig 82 and is traced.

Figure 13:
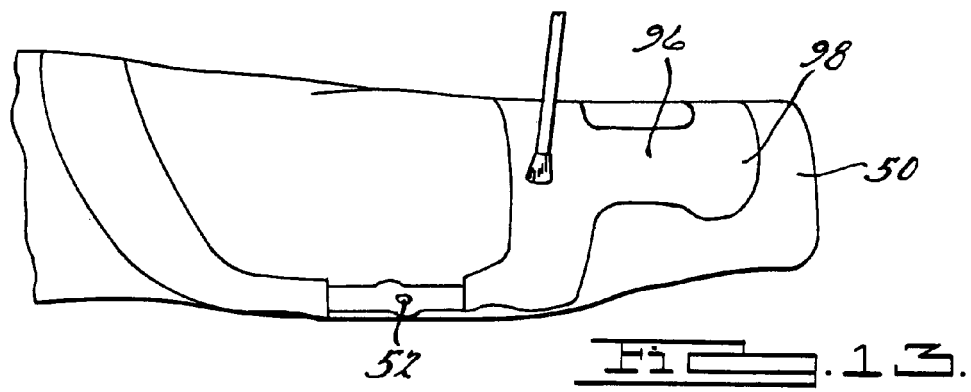

As is shown in FIG. 13, the flexible patterns 84 are removed from the cast model 50. Contact cement 96 is brushed inside the traced flexible pattern area 98 as well as metallic hinge jigs 82. The hinge jigs 82 are placed at the knee axis while the flexible thigh and calf patterns are positioned in their respective locations.

Figure 14:
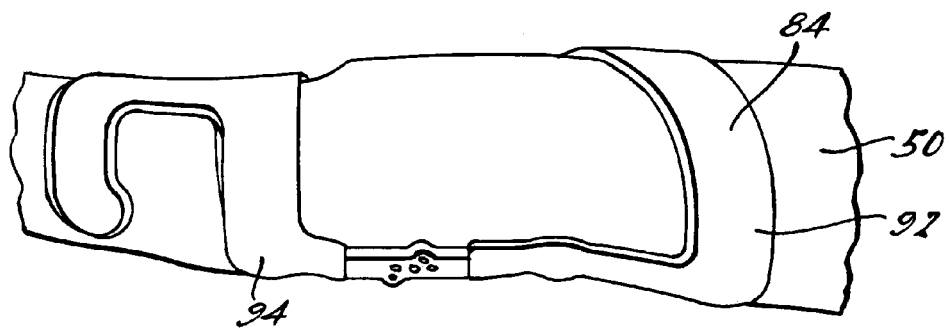
Figure 15:
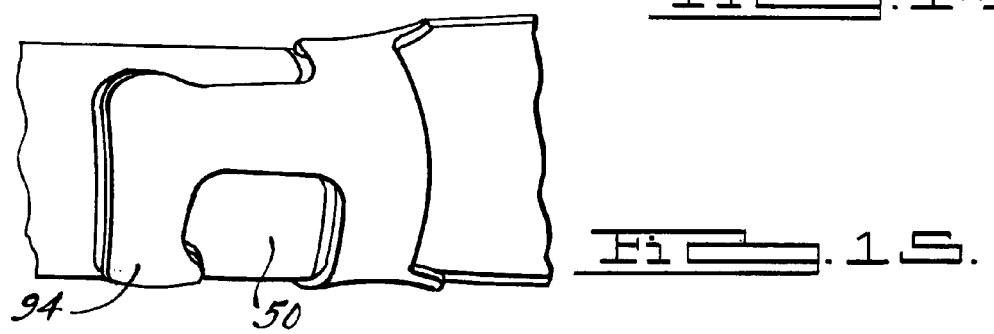

FIGS. 14 and 15 show the fixed flexible patterns 84. At this point, the flexible patterns 84 are checked for proper alignment, and the flexible calf pattern 94 is checked for proper tibia crest alignment. The flexible patterns 84 define the location of the three dimensional members, as well as the placement of hinges and mounting features.

FIG. 16 shows the initial step for producing the splash mold 90. Similar to the formation of the offset layer 78, a ⅛" sheet of polyethylene 100 is cleaned with alcohol and checked for defects. The polyethylene sheet 100 is then placed within a 400° F. oven 76. Two layers of stockinet 80 are again placed over the cast mold 50. In this regard, the stockinet 80 layers are placed over the flexible patterns 84. As is best shown in FIG. 16, the polyethylene sheet 100 is removed from the oven 76 after it turns clear (approximately 5 minutes) and placed over the cast model 50. The polyethylene sheet 61 is sealed on the ends 102 and the bottom 104. Vacuum is applied to the cast model through the mounting tube. Excess plastic is trimmed from the ends and the bottom of the polyethylene sheet 61. As is shown in FIG. 18, the thigh portion 104 and calf portion 106 of the splash mold 90 are labeled.

Figure 19:
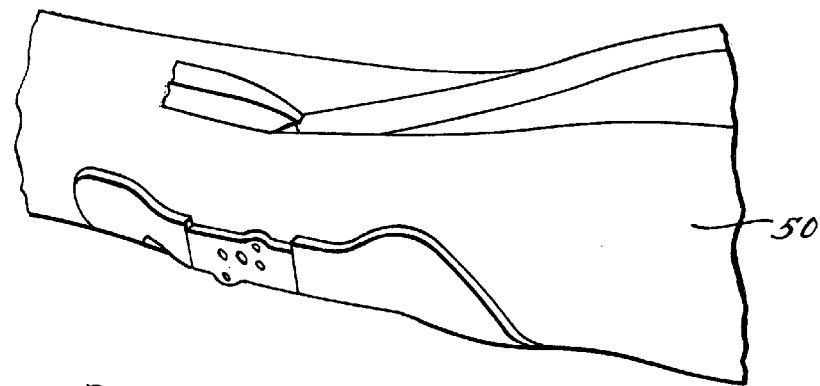
FIGS. 19-23 depict the removal of and preparation of the splash mold.

FIG. 19 shows the splash mold 90 being cut away from the casting along the back side of the cast model 50. The splash mold 90 is subsequently removed from the cast model 50. The flexible pattern 84 and stockinet 80 are subsequently removed from the cast model 50.

Figure 20:
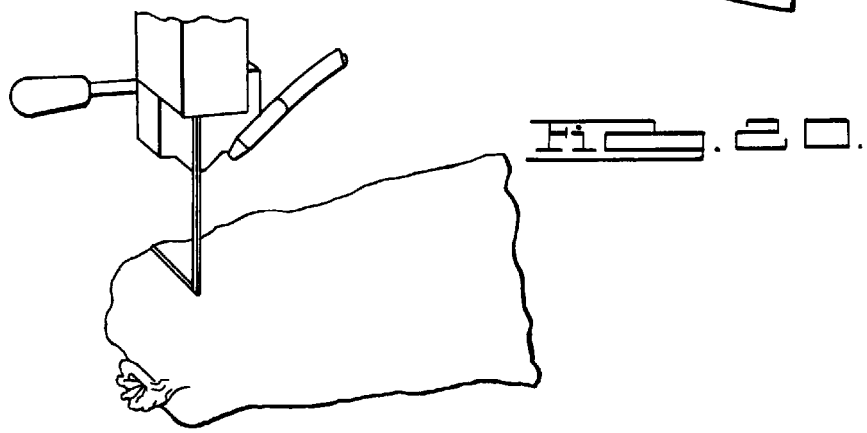
Figure 21:
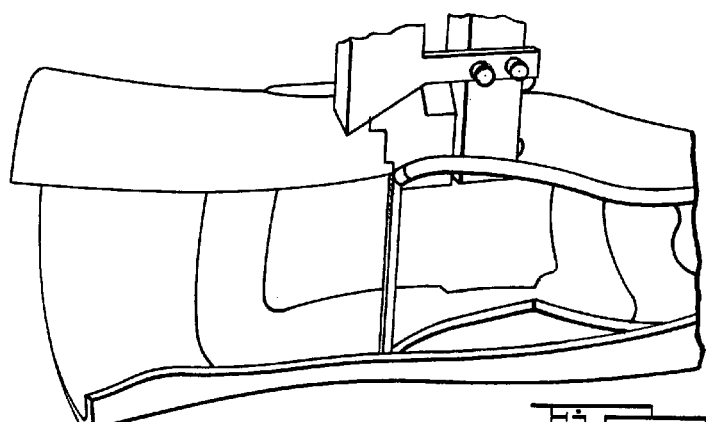
Figure 22:
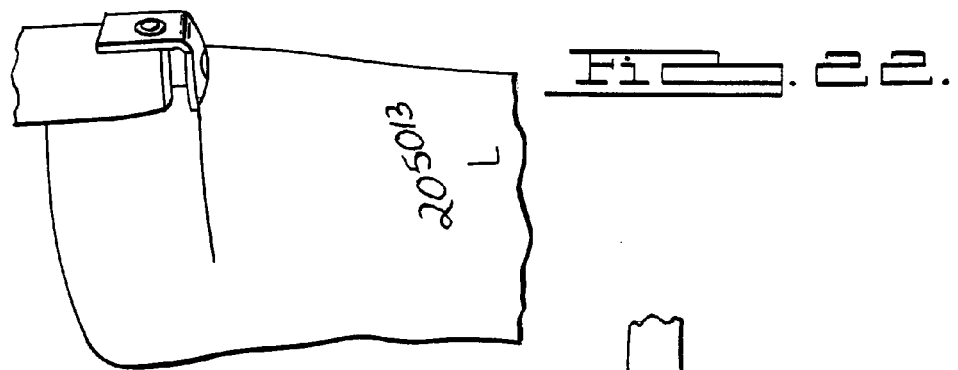
Figure 23:
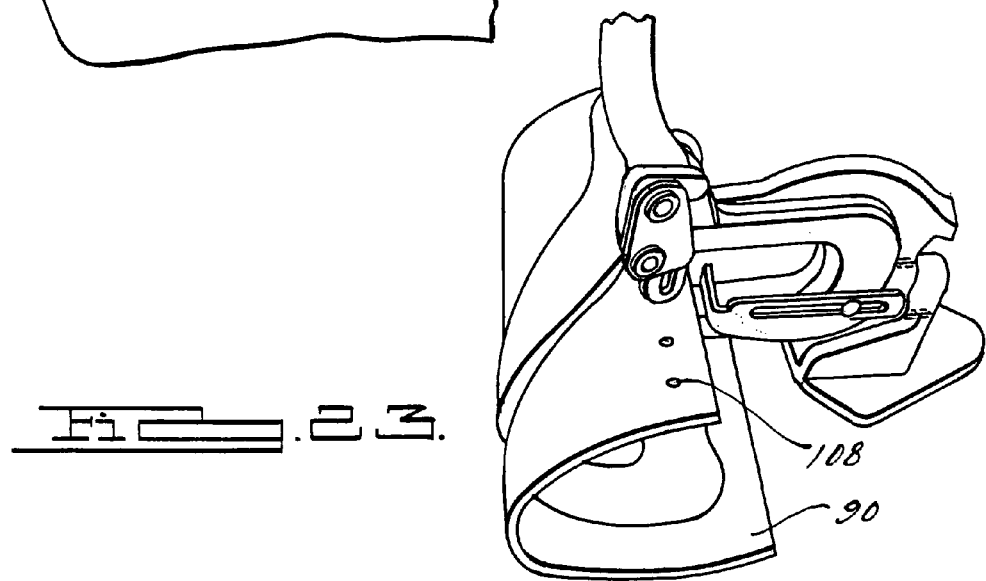

FIGS. 20-22 depict the preparation of the splash mold 90 for its use. Shown is the removal of excess polymer from the splash mold 90. FIG. 23 depicts the punching of mounting holes 108 in the outside periphery of the splash mold 90.

Figure 24:
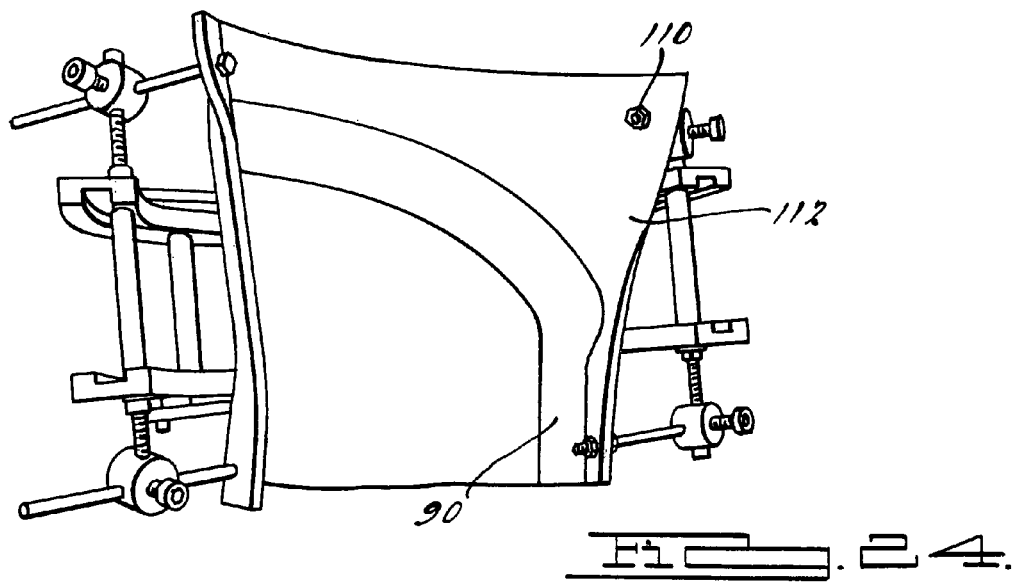
FIGS. 24-26 show the fixturing of the splash mold.
Figure 25:
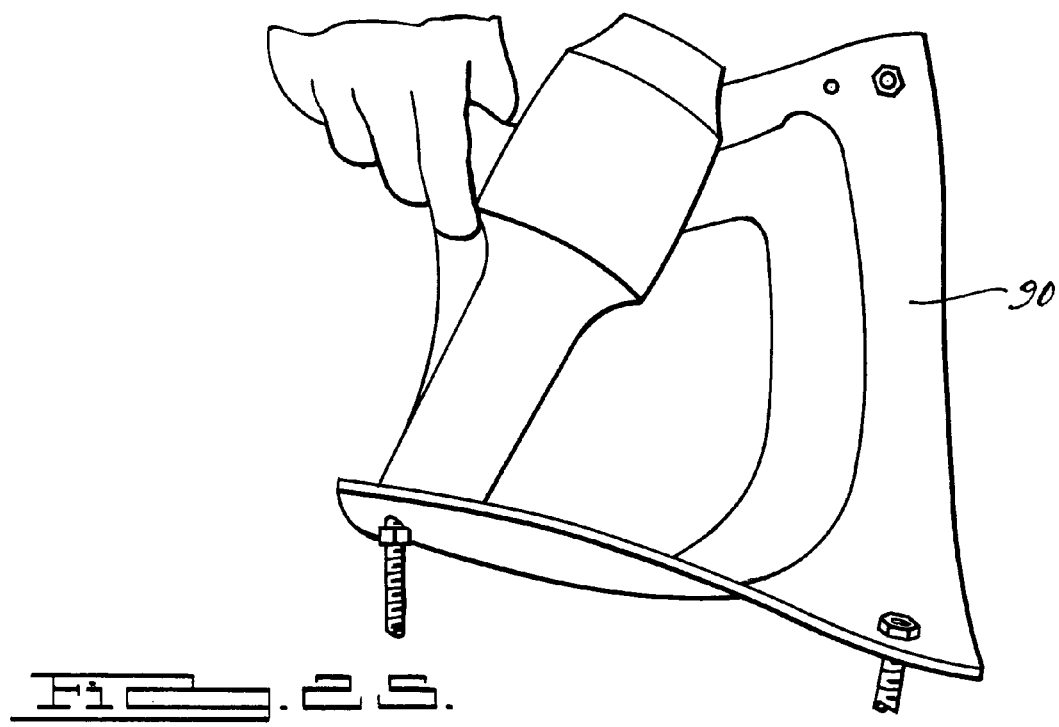

FIG. 24 depicts the fixturing of the splash mold 90. The splash mold 90 is shown being fixed by jig bolts through the mounting holes 108. Nuts 110 are placed onto the bolt and tightened to hold the splash mold 90 in place. The interior 112 of the mold is then cleaned with isopropyl alcohol which is evaporated using a heat gun as is shown in FIG. 25.

Figure 26:
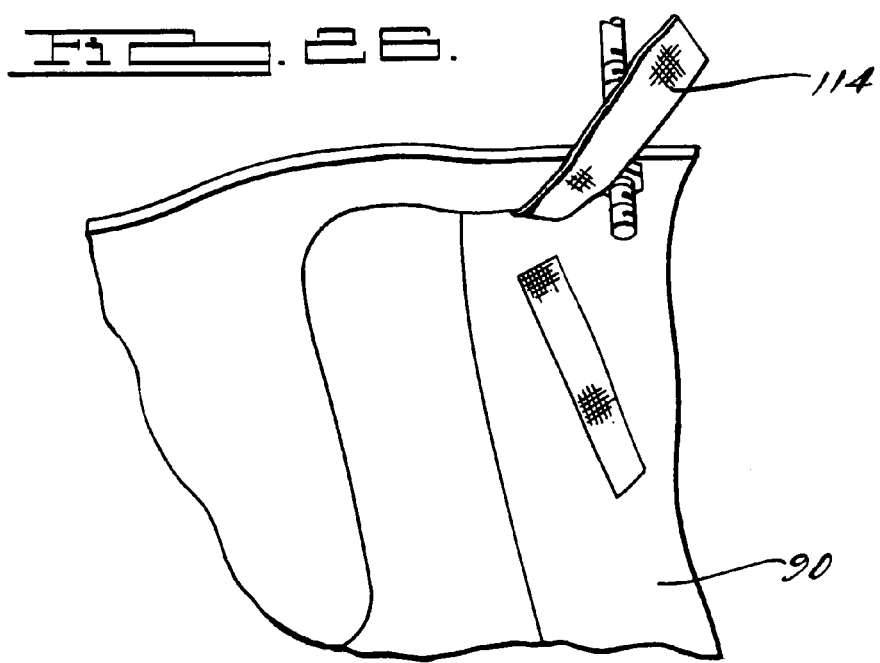
Figure 27:
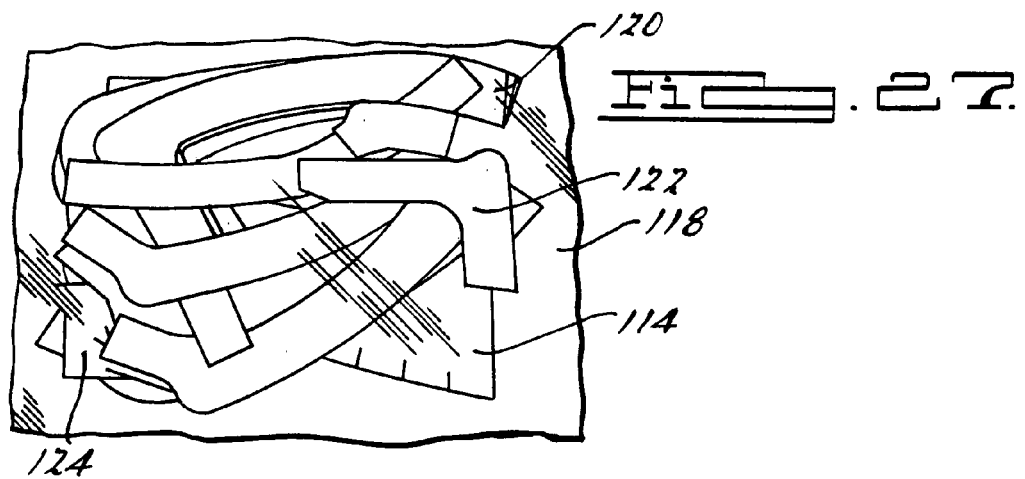
FIGS. 27 and 28 depict the composite pre-preg materials used to form the knee brace according to the teachings of the present invention.
Figure 28:
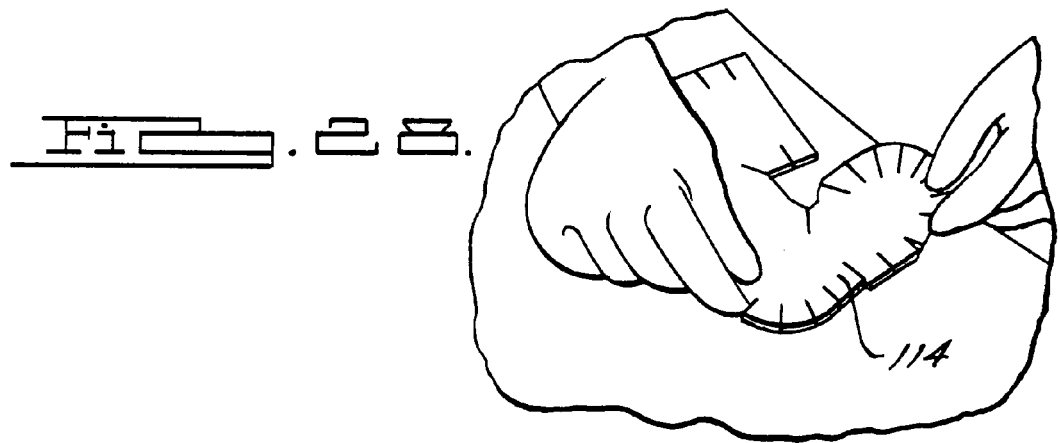

FIG. 26 depicts the application of carbon fiber starter strips 114 to the hinge area. Additionally, glass scrim 124 reinforcing material is applied to the hinge area 116. FIG. 27 depicts a prefabricated carbon fiber kit 118. The carbon fiber kit contains precut strips of a woven carbon fiber pre-preg material 120 and precut balsa wood core 122. The carbon fiber pre-preg material 120 is generally a very resin rich material. Preferably, having a 55% resin content is used in order to achieve a resin rich surface. The pre-preg material 120 is formed of woven carbon fiber. The fiber is preferably oriented in 90° and 60° orientations. Optionally, glass-fiber reinforced resin or KEVLAR reinforced resin can be used.

An example of the carbon fiber pre-preg material 120 are models DA 4090 and DA 4092 Modified Pre-Impregnated Systems available from Adhesive Pre-pregs for Composite Manufacturers of Plainsfield, Conn. This pre-preg material 120 is curable at 250° F. for 1 hour. The material has a tensile strength of about 63 ksi and flexural modulus of about $3 \times 10^6$ psi. The pre-preg material 120 optionally will have a curing cycle of 5-10° F. per minute temperature rise from room temperature to 180° F. while under a 25 Hg vacuum. Once at 180° F., 50 psi of pressure is applied to the exterior surface of the material and the temperature is increased at a rate of 5 to 10° F. per minute rise to 250° F. The construct is then held at 250° F. for one hour. Optionally, the pre-preg material 120 can be cured simply in an oven at 250° F. for about 10 hours under vacuum as opposed to in a pressurized autoclave.

Figure 29:
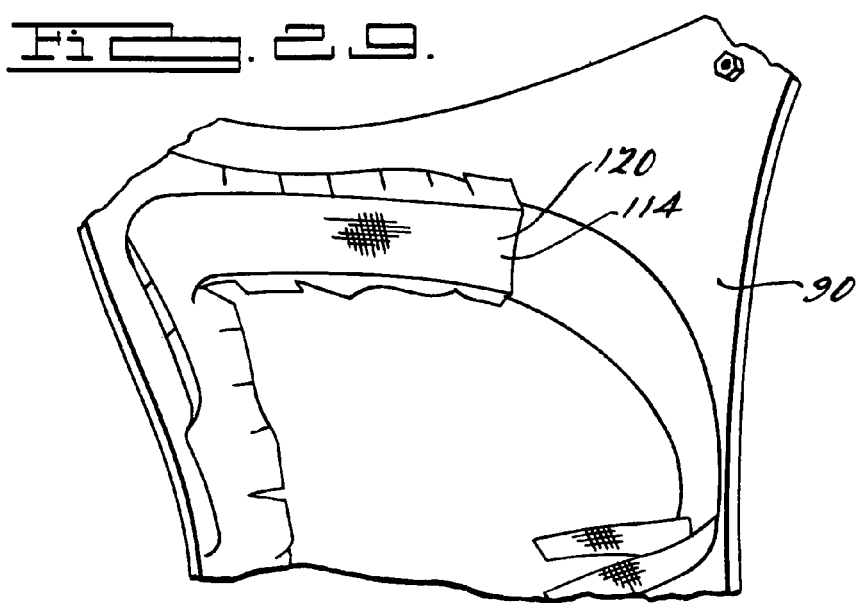
FIGS. 29 and 30 depict the application of woven pre-preg material and metal hinges into the cavity of the splash mold.

A glass scrim 124 layer is attached to a carbon fiber pre-preg material 120. FIG. 29 shows the placement of the first pre-preg layer 120 of carbon fiber with the glass scrim layer face down into the splash mold 90. The first pre-preg layer 126 is centered within the mold and pressed into position. A second pre-preg layer 128 with a 60° orientation is placed into the splash mold 90 with the adhesive side down.

Figure 30:
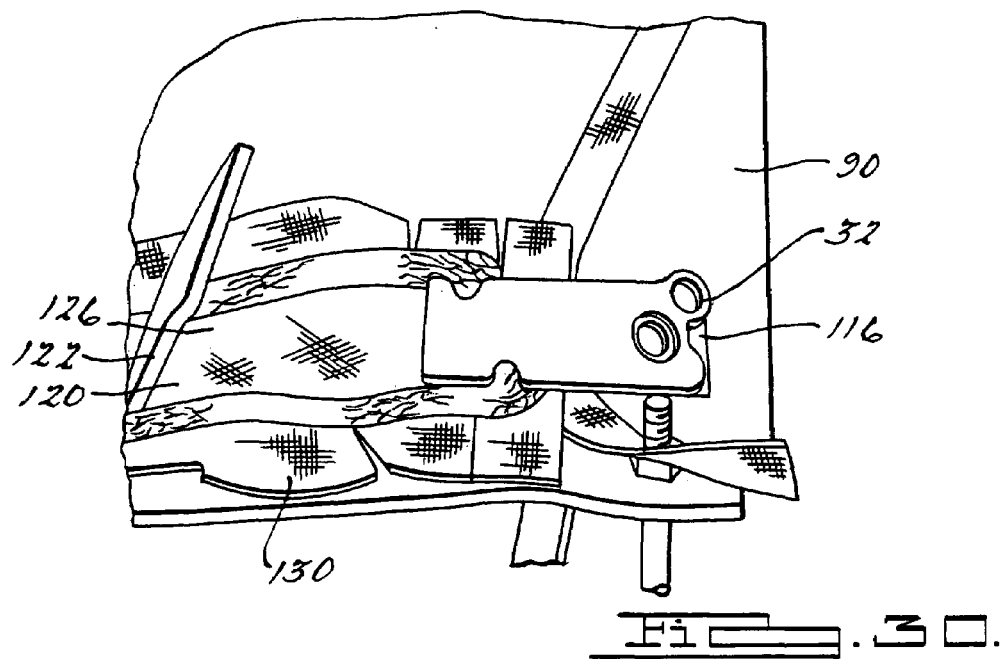

Next, a third pre-preg layer 130 having a 90° orientation is prepared and placed onto the splash mold 90 adhesive side down. With reference to FIG. 30, at this point, hinge bars 132 are identified for the splash mold 90 and placed into proper position.

Figure 31:
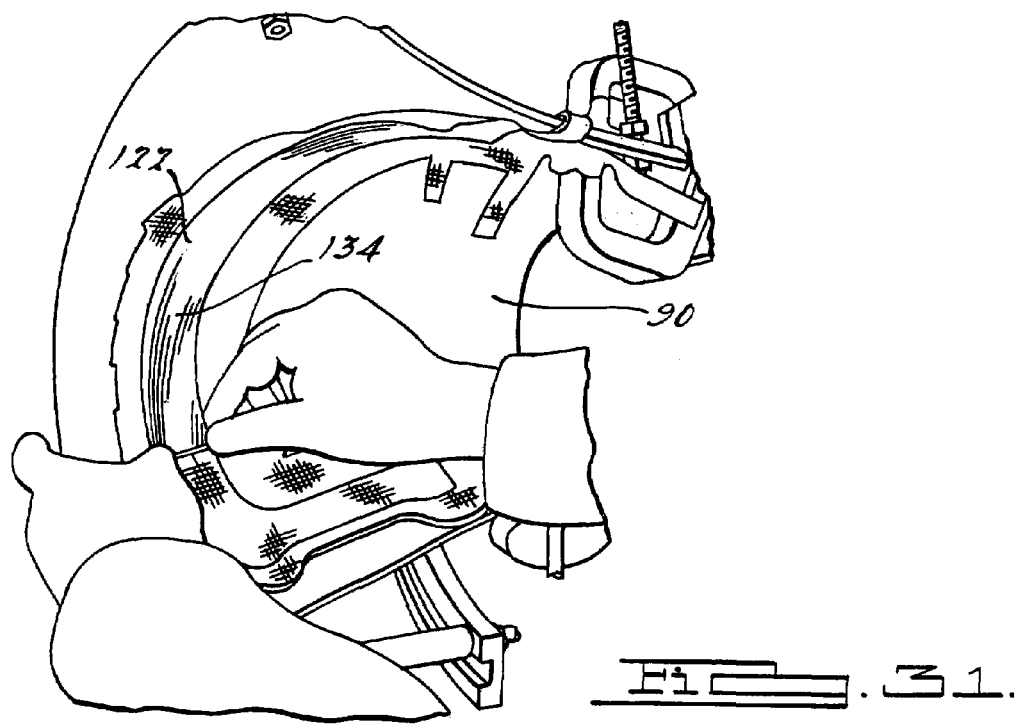
FIG. 31 shows the application of a balsa wood core according to the teachings of the present invention.

FIG. 31 depicts the insertion of the balsa wood core material 122 into the splash mold 90 with its mesh side 134 up. The core material is a scored balsa material 122 having a mesh backing. The excess core material is trimmed and removed.

Figure 32:
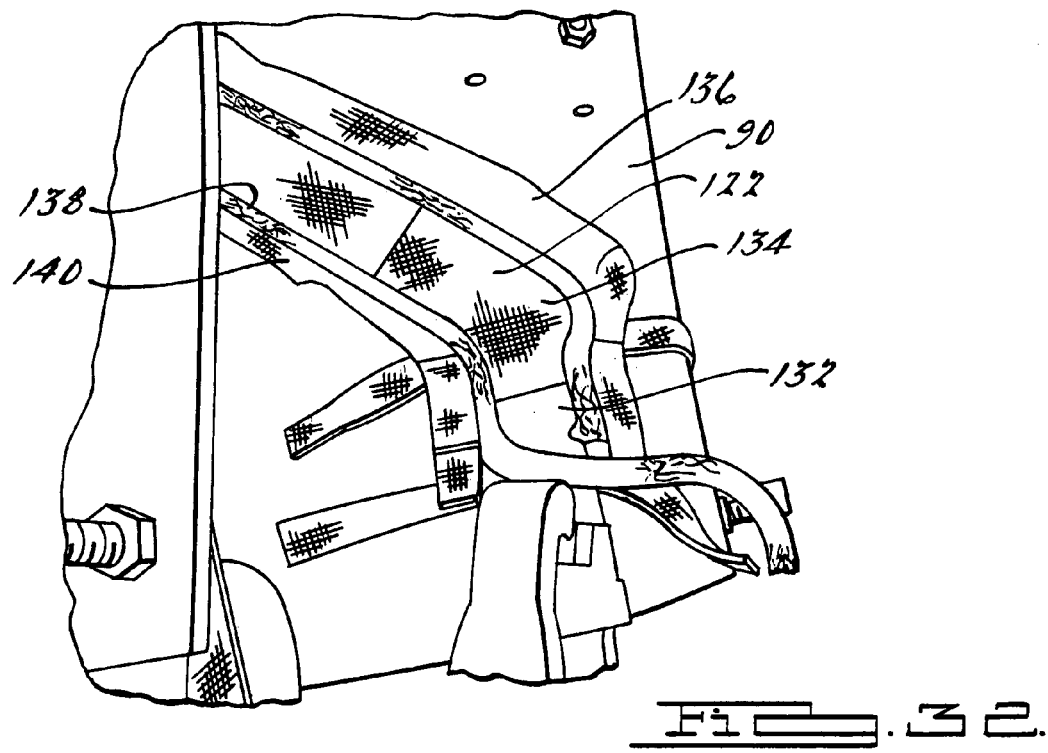
FIGS. 32 and 33 depict the application of a foam filler and carbon fiber cord into the composite construct.

FIG. 32 depicts the insert of carbon fiber braid material 136 into the hinge area. The braid material 136 is inserted between the outside edge 138 of the balsa wood core material 122 and the mold inside edge 140. The braid material 136 is applied to both the inside and outside edges from hinge to hinge 132.

Figure 33:
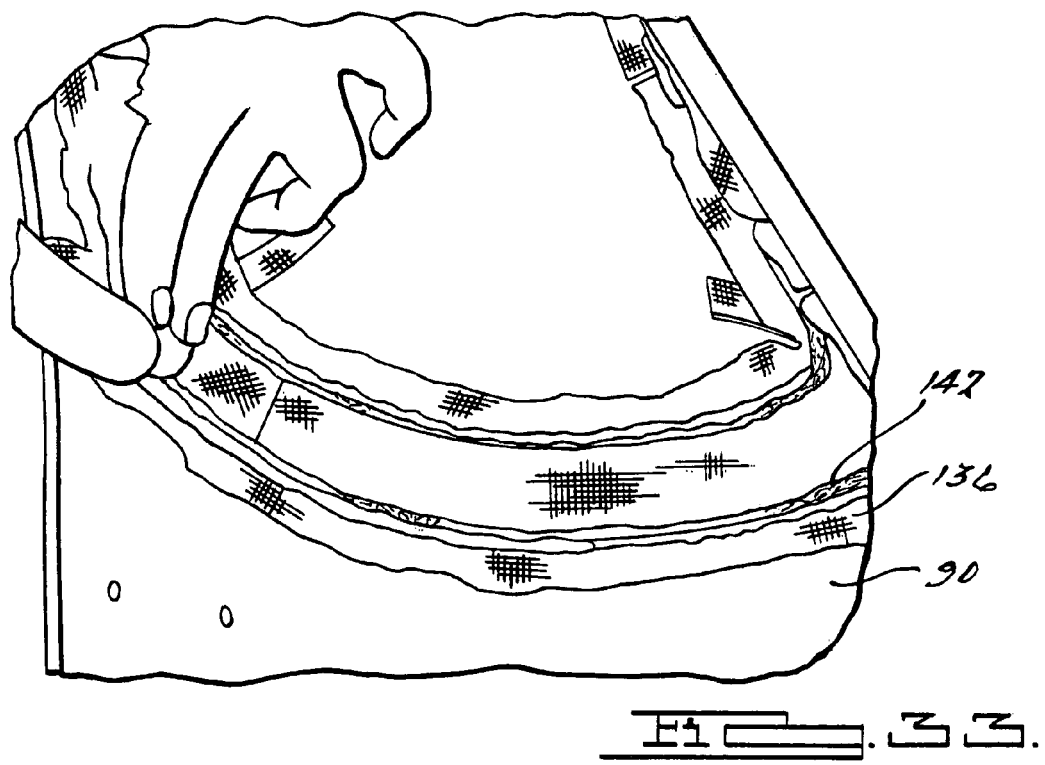

FIG. 33 shows the insertion of expanding foam 142 between the braid material and the mold edge. The expanding foam is cut into 0.25" strips. Any void surrounding the hinge is filled with expandable foam 142.

Figure 34:
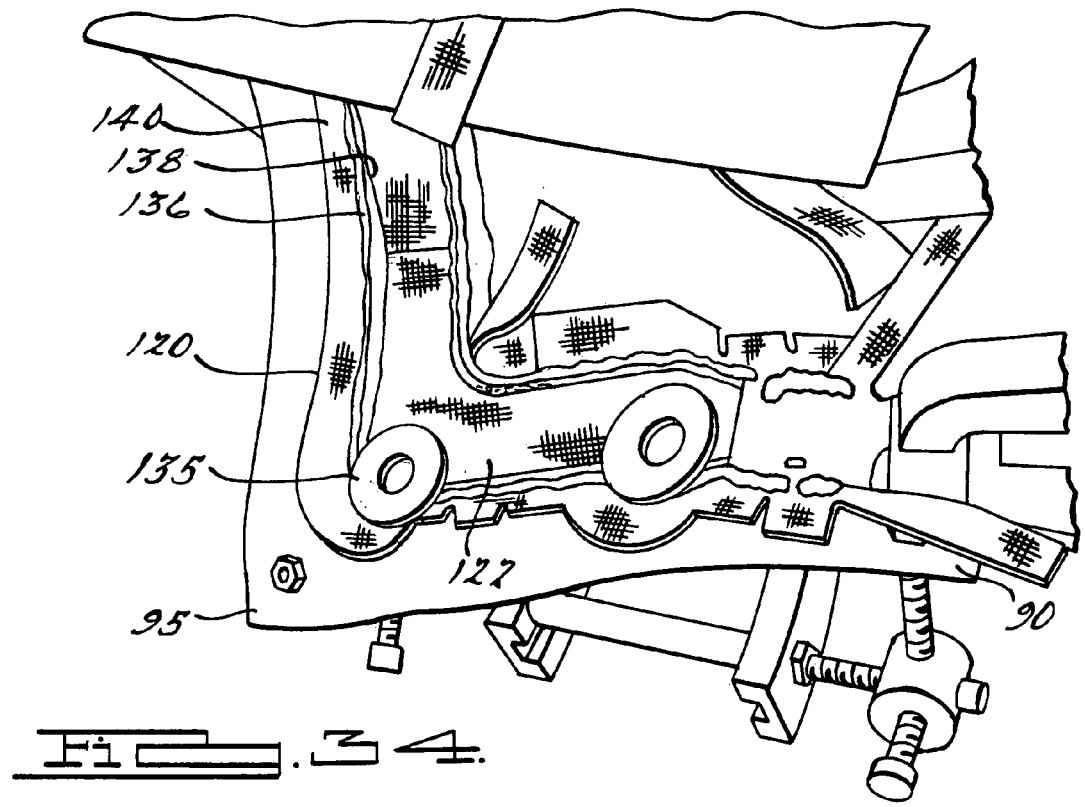
FIG. 34 depicts the application of steel washers into the composite structure.

FIG. 34 shows the application of metal washers 143 within the composite lay-up. These metal washers 135 are used as fixation points for the padding and harness (not shown) to be disposed within the three-dimensional frame 144.

Figure 35:
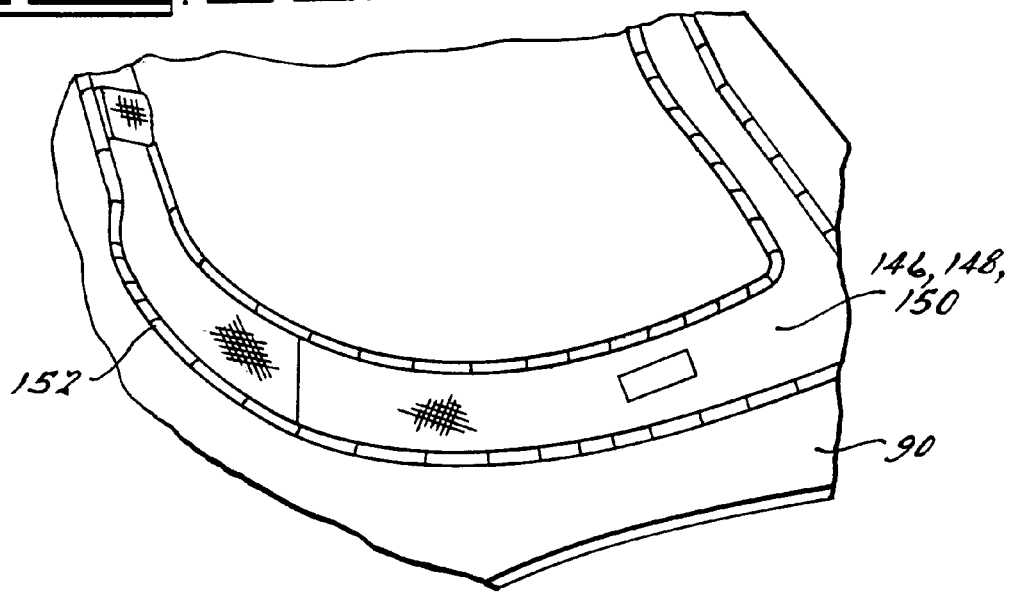
FIG. 35 depicts the application of woven pre-preg material to the splash mold.
Figure 36:
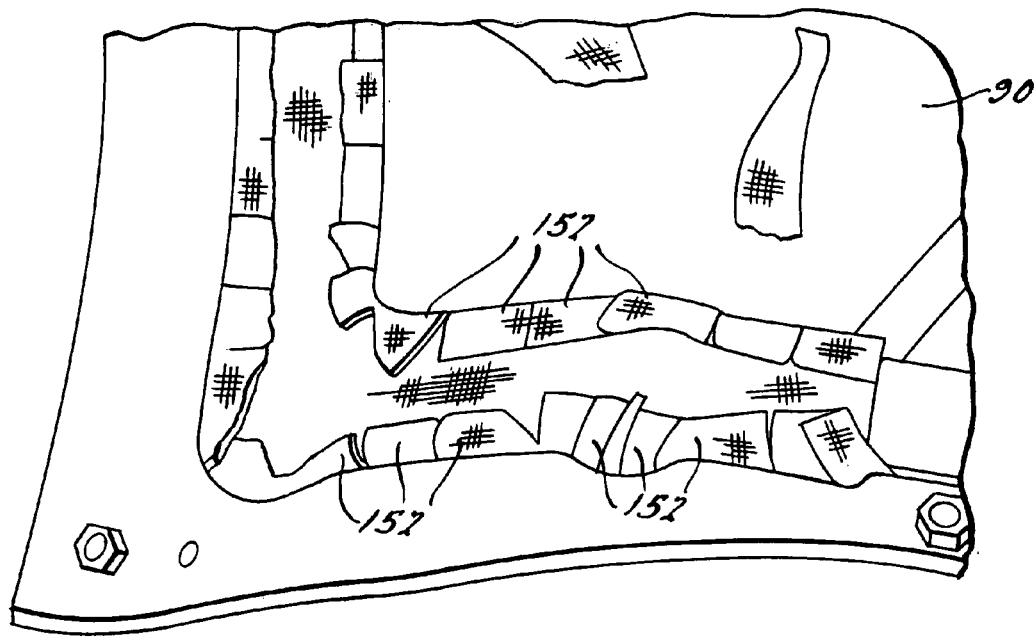
FIGS. 36-38 depict the edge preparation and subsequent application of a final layer according to the teachings of the present invention.

FIG. 35 shows the insertion of three layers of carbon fiber pre-preg (146, 148, 150). Specifically a 60° small layer 146 is placed into the mold adhesive side down. Next, a 90° carbon fiber layer 148 is placed into the mold adhesive side down. Lastly, a second 60° layer 150 is placed on top. FIG. 36 depicts folding bottom carbon fiber tabs 152 towards the center of the brace to enclose the pre-preg construct. The starter strips are folded towards the interior of the brace.

Figure 37:
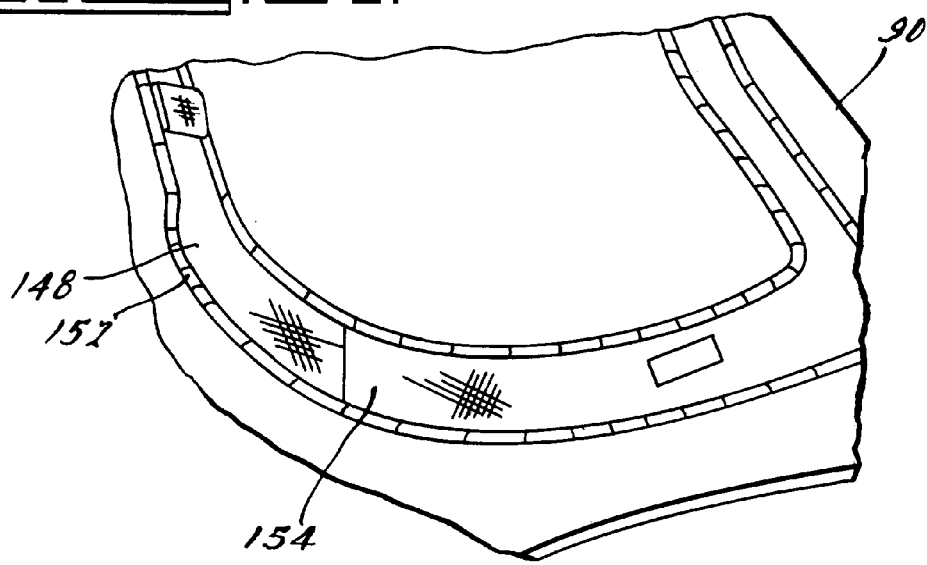
Figure 38:
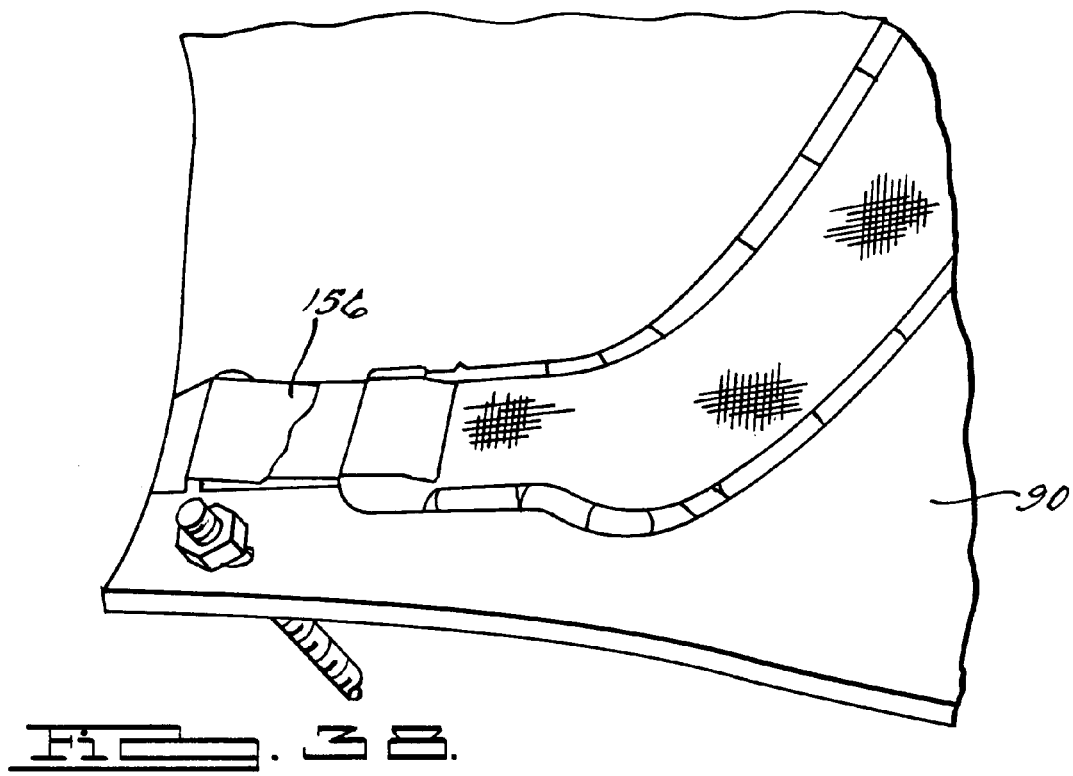
Figure 39:
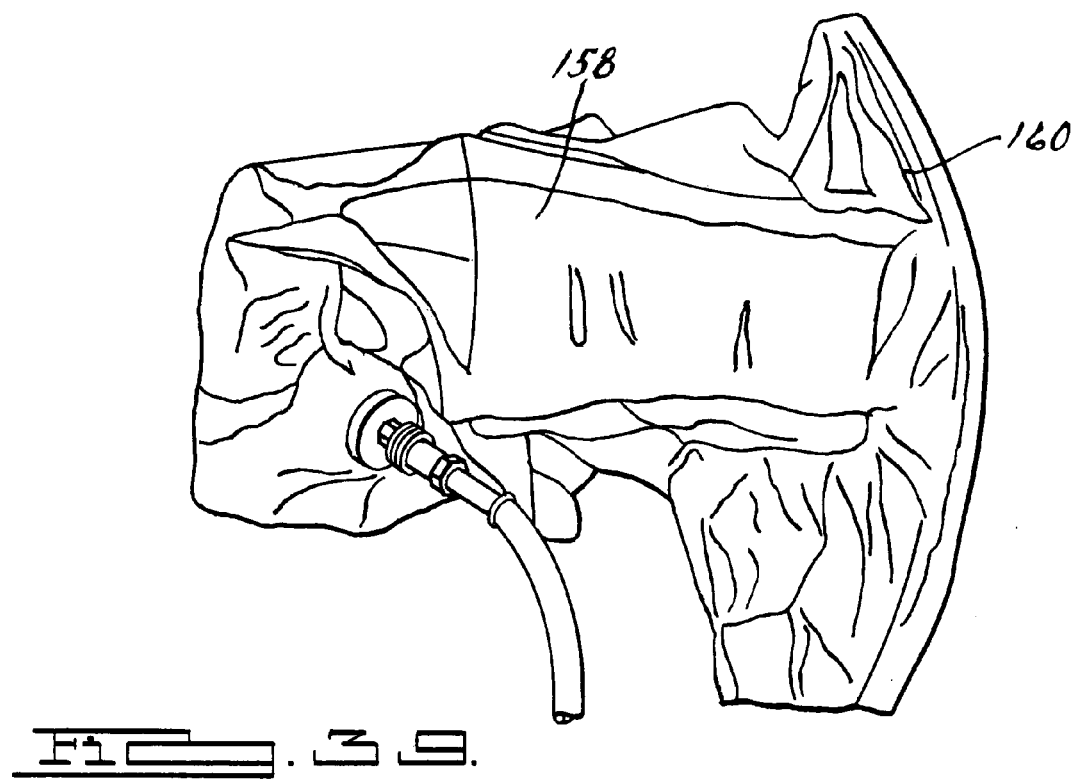
FIG. 39 depicts the use of a vacuum bag to remove air from between the layers of the uncured composite materials.
Figure 40A:
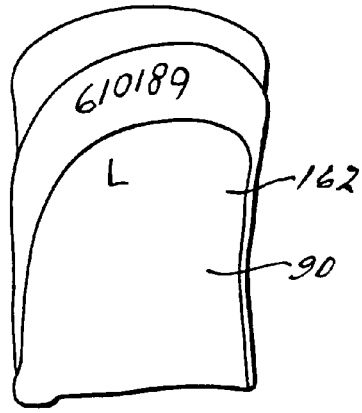
FIGS. 40a-40d depict the splash molds with uncured composites according to the teachings of the present invention.
Figure 40B:
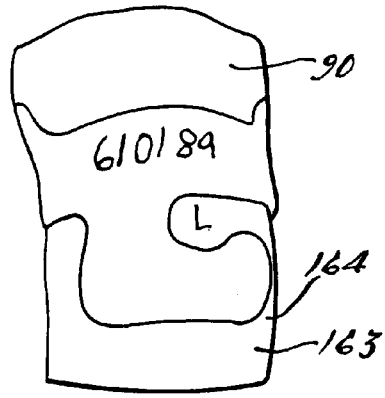
Figure 40C:
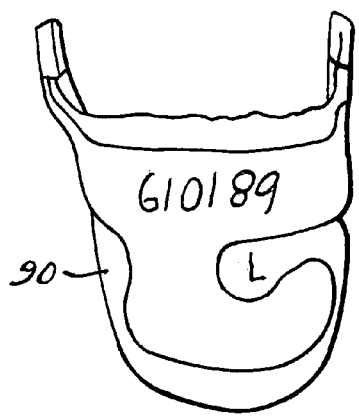
Figure 40D:
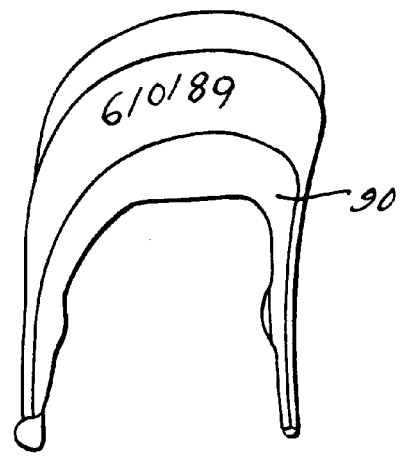

FIG. 37 depicts the application of another layer 154 of 90° orientated fibers over the composite covering the folded tabs. FIG. 38 depicts the folding of the hinge starter strip 156 inward to form a straight seam along the hinge. As best seen in FIG. 39, the entire assembly 158 is placed within a rubber bag 160 and a vacuum is pulled on the splash mold 90 for 15 minutes to remove as much air as possible from between the pre-preg laminate layers.

Figure 41:
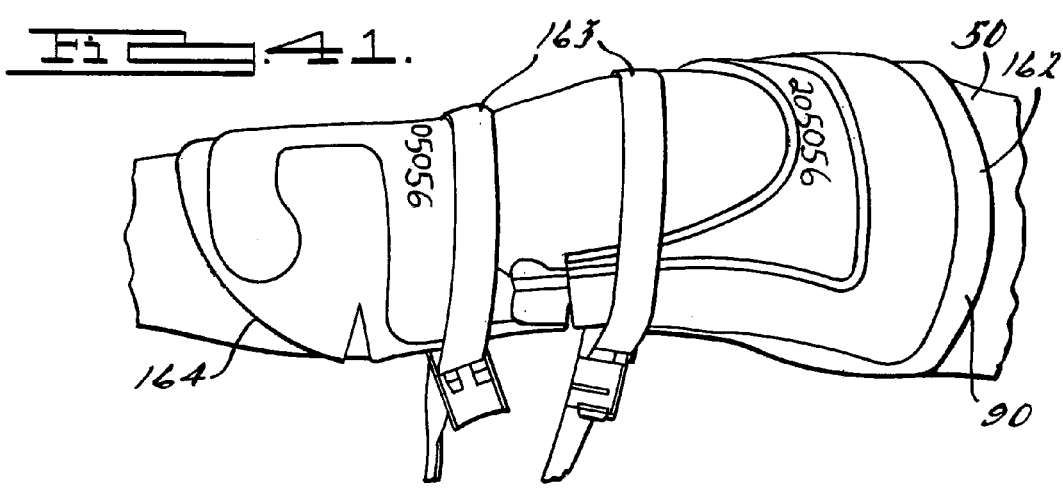
FIG. 41 depicts the application of the uncured splash molds onto the offset layer of the plaster cast according to the teachings of the present invention.
Figure 42:
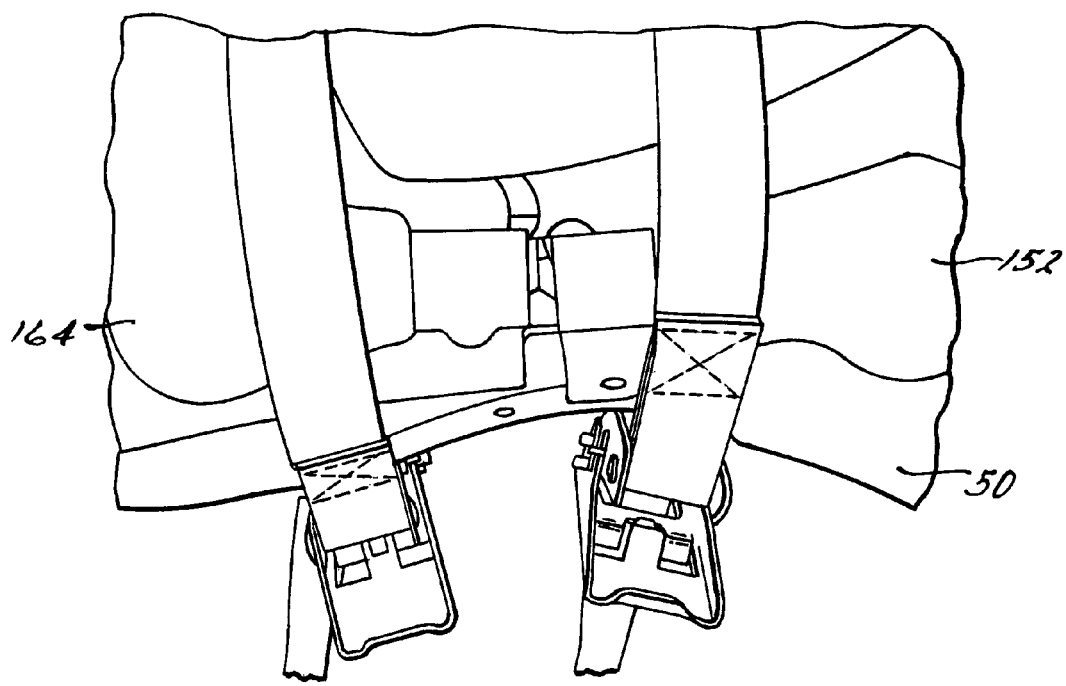
FIGS. 42 and 43 show the preparation of the hinge area prior to autoclaving.

FIGS. 40a-40d show the filled splash molds 90 after they are removed from the rubber bag 160 and are trimmed using a manual cutter. FIG. 41 shows the packed thigh mold 162 being positioned onto the cast Model 50. Straps 163 are used to hold the thigh mold 162 into position. Next, the packed calf mold 164 is positioned onto the cast model 50 and a strap 163 is used to hold the padded calf mold 164 into position. In FIG. 42, a utility knife is used to trim the thigh and calf molds 152 and 164 away from the hinge areas.

Figure 43:
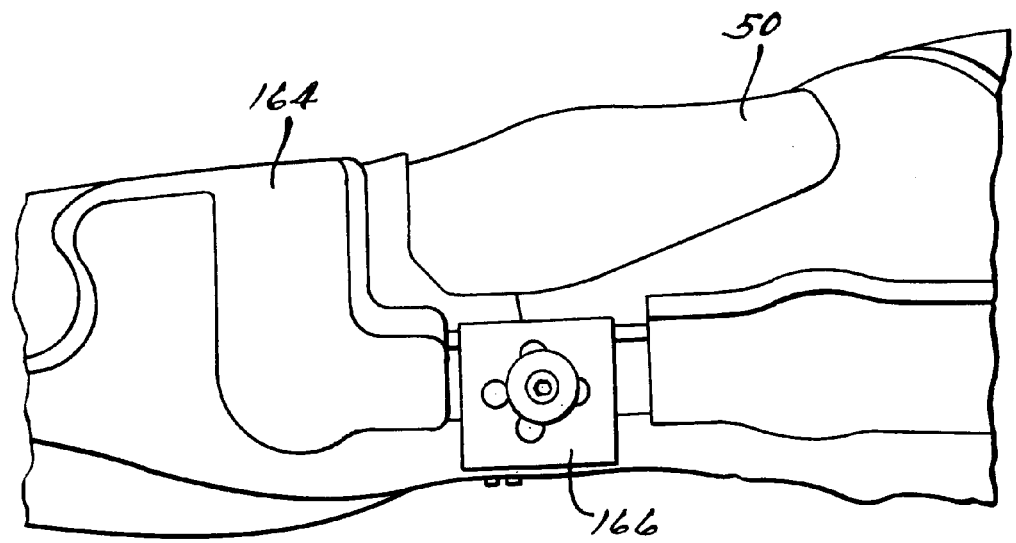
Figure 44:
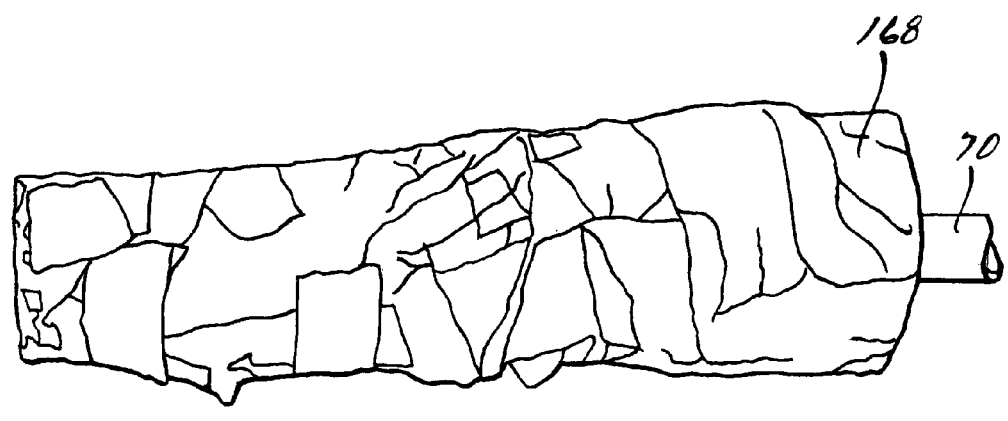
Figure 45:
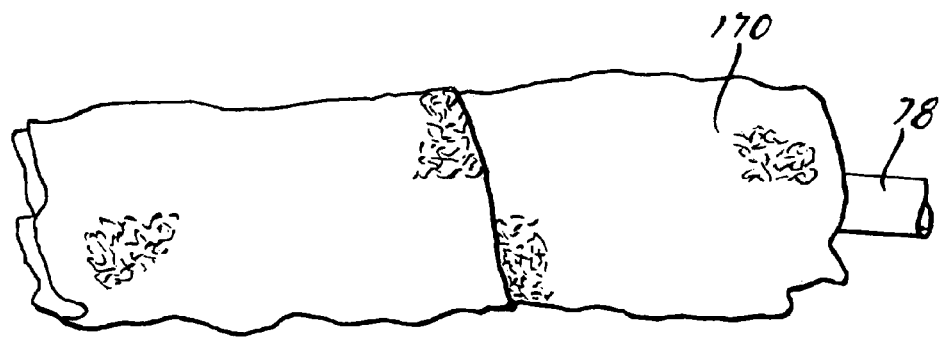
Figure 48:
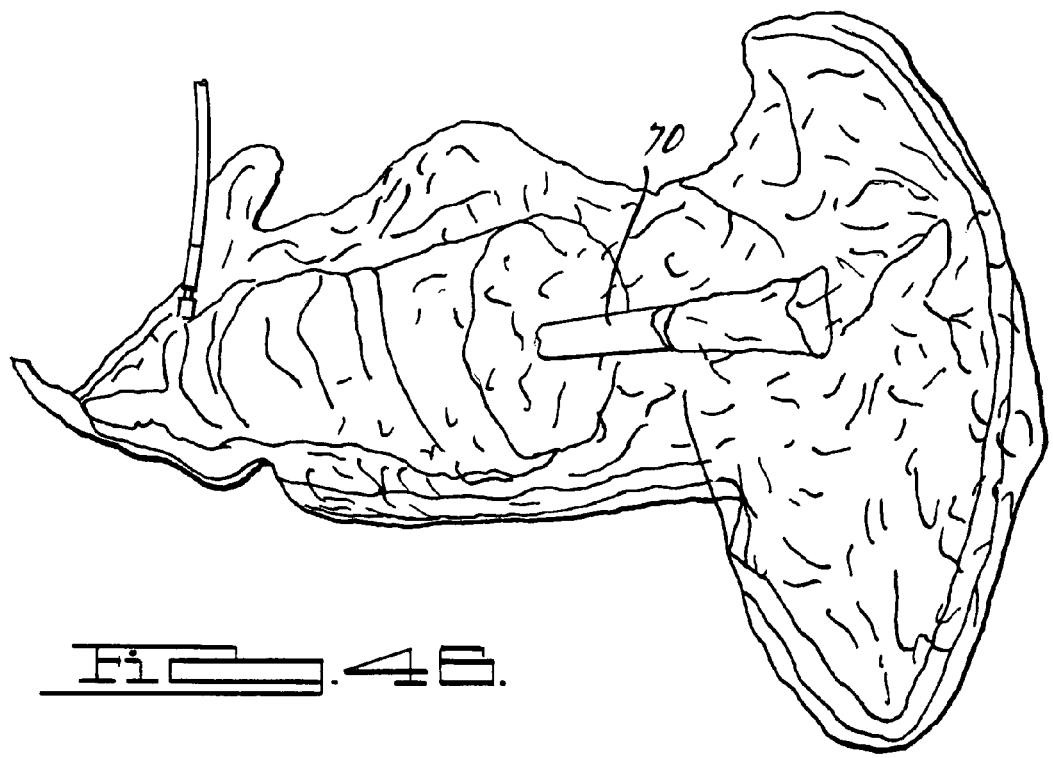

FIG. 43 shows the hinges being applied to the calf side 164 of the uncured structure. The hinges 166 are secured to both sides of the brace using hinge holders (not shown). FIG. 44 depicts the assembly being wrapped with rubber material 168 while FIG. 45 shows the assembly now being wrapped with breather material 170 which is used to degas the structure while it is being processed. At this point, the rubber sealing member 72 is again placed onto the aluminum supporting member 72. A portion of the breather material 170 is placed under the rubber sealing member to ensure proper gas flow during the processing of the material. The assembly is then placed within a vacuum bag 172 and sealed using sealing tape. A vacuum is then applied to check for leaks with any leaks being sealed.

The entire assembly is then placed into an oven 76 with a vacuum line attached to the vacuum hose. The construct is cured for ten hours at an oven temperature of 250° F.

Figure 47:
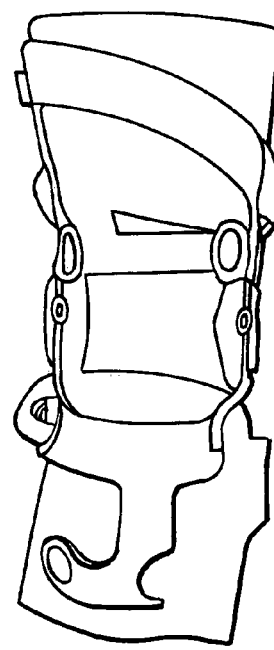
FIG. 47 depicts a three-dimensional knee brace produced according to the teachings of the present invention.

FIG. 47 discloses a brace produced according to the process of the present invention. A significant advantage of the present system is the ability to produce a customized three-dimensional composite structure without using metal tooling plates. The splash mold 50 functions as a thermoplastic pressure plate. Of particular note is the ability to use a polyethylene thermoplastic sheet as a pressure plate/mold without the use of release film or release materials.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A method of producing a three-dimensional composite support structure for supporting a body comprising the steps of:
   a) providing a three-dimensional model of the body;
   b) coupling a flexible pattern to a portion of the model;
   c) covering the body model and flexible pattern with a deformable thermoplastic polymer layer;
   d) applying one of pressure or vacuum to the thermoplastic polymer layer so as to cause an imprint of the flexible pattern to be formed into the polymer layer;
   e) allowing the thermoplastic polymer layer to harden into a splash mold;
   f) removing the splash mold from the body model and flexible pattern;
   g) removing the flexible pattern from the model;
   h) applying reinforced polymer into the imprint of the flexible pattern in the splash mold;
   i) coupling the splash mold containing the reinforced polymer to the model of the body; and
   j) applying at least one of pressure or vacuum to the model and the splash mold in the presence of heat so as to form the reinforced polymer material.

2. The method according to claim 1 further including the step of coupling a breather layer over the body model.

3. The method according to claim 1 wherein providing a body model is providing a cast model of the body.

4. The method according to claim 1 further comprising the step of providing one of cutouts, landmarks and fixation points on the surface of the model.

5. The method according to claim 1 wherein providing a model of a body is providing a model created utilizing a bio-scan system.

6. The method according to claim 1 further including coupling metallic component to the reinforced polymer.

7. The method according to claim 6 wherein coupling a metallic component is coupling a metallic component prior to forming of the reinforced polymer.

8. The method according to claim 6 wherein applying reinforced polymer into the imprint is applying reinforced thermoset pre-preg into the imprint.

9. The method according to claim 8 wherein the step of applying reinforced polymer material is applying reinforced thermoset pre-preg material having an alternating orientation.

10. The method according to claim 1 further comprising the step of placing a deformable thermoplastic polymer spacer layer over a portion of the body model prior to the coupling of the flexible pattern.

11. The method according to claim 1 further comprising the step of placing a breather material over the flexible pattern prior to covering the body model and flexible pattern with a deformable thermoplastic polymer layer.

12. The method according to claim 1 further comprising the step of placing the splash mold including reinforced polymer into a vacuum bag and applying one of pressure or a vacuum to remove air from the reinforced material.

13. A method for producing a custom knee brace comprising the steps of:
   a) providing a three-dimensional model of a knee;
   b) coupling a flexible pattern corresponding to a portion of the knee brace to the surface of the knee model;
   c) covering the knee model and flexible pattern with a deformable thermoplastic polymer layer;
   d) applying one of pressure or a vacuum to the thermoplastic polymer layer so as to cause an imprint of the flexible pattern into the thermoplastic polymer layer;
   e) allowing the thermoplastic polymer layer to harden into a splash mold;
   f) removing the splash mold from the model of the knee;
   g) applying reinforced thermoset polymer prepreg to the imprint of the flexible model of the splash mold;
   h) coupling the splash mold to the model of the knee; and
   i) applying one of pressure or vacuum to the splash mold in the presence of heat so as to cure the reinforced polymer material.

14. The method according to claim 13 further comprising the step of coupling a metal hinge to the reinforced thermoset polymer pre-preg.

15. The method according to claim 14 wherein coupling a metallic hinge to the reinforced thermoset polymer pre-preg is coupling a metallic hinge to the reinforced material prior to curing of the reinforced thermoset polymer pre-preg.

16. The method according to claim 13 further comprising the steps of positioning at least one stockinet over the knee cast prior to the coupling of the flexible pattern.

17. The method according to claim 13 further comprising the steps of coupling a polymer offset layer to the knee model prior to the coupling of the flexible pattern.

18. The method according to claim 17 wherein the coupling of an offset layer is the coupling of a heated thermoplastic polymer layer by use of one of vacuum or pressure.

* * * * *